United States Patent [19]

Kazlauskas

[11] 4,455,420

[45] Jun. 19, 1984

[54] 4-AMINO-7-(5-DEOXY-BETA-D-RIBOFURANOSYL)-5-IODO-7H-PYRROLO[2,3-d] PYRIMIDINE

[75] Inventor: Rymantas Kazlauskas, Cromer, Australia

[73] Assignee: Hoffmann-La Roche Inc., Nutley, N.J.

[21] Appl. No.: 457,598

[22] Filed: Jan. 13, 1983

[51] Int. Cl.³ .............................................. C07H 17/00
[52] U.S. Cl. ....................................... 536/24; 424/180
[58] Field of Search ........................................... 536/24

[56] References Cited

U.S. PATENT DOCUMENTS 3,299,042  1/1967  Lipkin .................................. 536/24
4,140,851  2/1979  Townsend ............................. 536/24

OTHER PUBLICATIONS

Chemical Abstracts 98:140811 (1983).

*Primary Examiner*—Ethel G. Love
*Attorney, Agent, or Firm*—Jon S. Saxe; Bernard S. Leon; Alan R. Stempel

[57] ABSTRACT

A compound, 4-Amino-7-(5-deoxy-beta-D-ribofuranosyl)-5-iodo-7H-pyrrolo[2,3-d] pyrimidine, as well as process to produce this compound, are disclosed. The compound is useful as a muscle relaxant.

2 Claims, No Drawings

4-AMINO-7-(5-DEOXY-BETA-D-RIBOFURANOSYL)-5-IODO-7H-PYRROLO[2,3-D]PYRIMIDINE

DESCRIPTION OF THE INVENTION

The invention relates to a hitherto unknown pyrrolo[2,3-d]pyrimidine derivative, namely 4-Amino-7-(5-deoxy-beta-D-ribofuranosyl)-5-iodo-7H-pyrrolo[2,3-d]pyrimidine; that is, a compound having the structural formula:

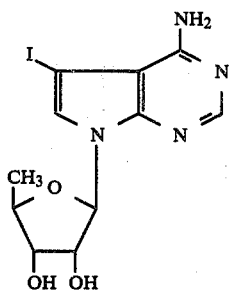

In accordance with the invention it has been found that 4-Amino-7-(5-deoxy-beta-D-ribofuranosyl)-5-iodo-7H-pyrrolo[2,3-d]pyrimidine is contained in low quantities in red algae of the species Hypnea valendiae. Further, it has been found that this compound can be isolated from this algae so as to exist in substantially pure form, that is, in a form substantially free of naturally occuring by-products. Accordingly, the invention relates most specifically to the isolation of 4-Amino-7-(5-deoxy-beta-D-ribofuranosyl)-5-iodo-7H-pyrrolo[2,3-d]pyrimidine and to this compound in substantially pure form.

As can be seen from the examples which follow, the isolation of 4-Amino-7-(5-deoxy-beta-D-ribofuranosyl)-5-iodo-7H-pyrrolo[2,3-d]pyrimidine can be accomplished using known per se extraction and purification techniques.

Although not considered to be part of the invention, 4-Amino-7-(5-deoxy-beta-D-ribofuranosyl)-5-iodo-7H-pyrrolo[2,3-d]pyrimidine can be prepared synthetically, as well, by a method also described in the examples.

4-Amino-7-(5-deoxy-beta-D-ribofuranosyl)-5-iodo-7H-pyrrolo[2,3-d]pyrimidine has various pharmacological or therapeutical activities. The compound has been found to act as a muscle relaxant and to produce a reduction in body temperature in mice. It has also been found to be a potent inhibitor of adenosine kinase from rat and guinea pig brain.

A suitable pharmaceutical dosage form utilizes about 5 mg/kg to about 50 mg/kg and preferably about 20 mg/kg daily of 4-Amino-7-(5-deoxy-beta-D-ribofuranosyl)-5-iodo-7H-pyrrolo[2,3-d]pyrimidine. It should be understood, however, that the dosage administration to a particular patient is variable and depends upon the clinician's judgment, using as the criteria the condition and sixes of the patient and the patient's response thereto.

The compound may be incorporated in an oral dosage form such as tablets, capsules or elixers or in an injectable form in a sterile vehicle wherein the compound is soluble and prepared to conventional pharmaceutical methods.

The nature and objects of the present invention can be more fully understood by making reference to the following examples.

EXAMPLE 1

Red algae of the species Hypnea valendiae was collected at Quobba Lagoon, Western Australia. From this, a crude methanol extract was prepared in a conventional manner. The extract, when administered to mice, was found to produce pronounced muscle relaxation and hypothermia and, in addition, to block polysynaptic and monosynaptic reflexes.

Fractionation of the crude extract, on florisil, followed by purification by h.p.l.c. monitored by muscle relaxation and hypothermia in mice, produced a single crystalline compound responsible for all observed pharmacological activities. The formula $C_{11}H_{13}IO_3N_4$ was established by high resolution mass spectrometry and a base peak at m/e 260 ($C_6H_5IN_4$) suggested that the compound was a nucleoside of a deazapurine base. The $^1H$ n.m.r. spectrum (100 MHz) of the compound in deuteropyridine showed reasonances at $\delta 8.48$ (1H,S), 7.64 (1H,S), and 7.24 (2H,S), disappearing on addition of $D_2O$, attributable to an aminodeazapurine. Additional reasonances at $\delta 6.80$ (1H, d, J 4 Hz), 4.76 (1H, t, J 4 Hz), 4.40 (2H, m), and 1.52 (3H, d, J 7 Hz) were assigned to a 5-deoxypentose sugar.

The $^{13}C$ n.m.r. spectrum of the compound showed reasonances at 156.9 (s), 151.9 (d, J 198 Hz), 150.1 (S), 126.7 (dd, J 193.5, 5.4 Hz), 103.4 (S), 86.9 (d, 164 Hz), 79.2 (d, 152.6 Hz) 74.4 (d, 145 Hz), 73.3 (d, 148 Hz), 52.1 (d, 4.9 Hz) and 18.9 (q. 123.9 Hz) ppm.

On the basis of the above data, the following structure was assigned to the isolated product:

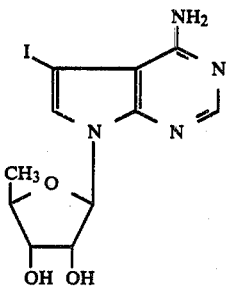

EXAMPLE 2

A crude methanol extract of a fresh collection of the algae of Example 1 was prepared. Fractionation of this new extract gave fewer active fractions and a much smaller yield of 4-Amino-7-(5-deoxy-beta-D-ribofuranosyl)-5-iodo-7H-pyrrolo[2,3-d]pyrimidine than obtained in Example 1. Final h.p.l.c. purification of the extract yielded mainly a biologically less active isomer which is suspected to be epimeric, with respect to the compound obtained in Example 1, at the carbon of the sugar-base junction of the nucleoside.

EXAMPLE 3

Synthesis of 4-Amino-7-(5-deoxy-beta-D-ribofuranosyl)-5-iodo-7H-pyrrolo[2,3-d]pyrimidine.

A solution of 2.27 g of mercuric acetate in 50 ml. water was added dropwise to a mixture of 1.78 g of 7-[5-deoxy-beta-D-ribofuranosyl)7H-pyrrolo[2,3-d]pyrimidin-4-amine [K. Anzai and M. Matsui, Bull.

Chem. Soc. Japan 46, 618-623 (1973)], 2.9g of sodium acetate and 175 ml. of water at 65° C. The reaction was stirred vigorously under a nitrogen flow and maintained at 65° for four hours. The mixture was neutralized with 15 ml. of one normal ammonium hydroxide, cooled to room temperature and filtered. The precipitate was washed with 2×50 ml. of water, 2×50 ml. of methanol, 2×50 ml. of ether and dried in vacuum over phosphorous pentoxide to yield 2.85 g. (85%) of 7-(5-deoxy-beta-D-ribofuranosyl)-5-mercuri-7H-pyrrolo[2,3-d]pyrimidin-4-amine as an amorphous solid.

A suspension of 2.63 g. of 7(5-deoxy-beta-D-ribofuranosyl)-5-mercuri-7H-pyrrolo[2,3-d]pyrimidin-4-amine was treated with 1.7 g. of iodine in 25 ml. of dimethylformamide for six hours at room temperature. The solution was then evaporated to an oil, extracted with 3×50 ml. of methanol and filtered. Forty grams of silica gel were added to the methanolic filtrate and evaporated to dryness. Chromatography of this material on a 500 g. column of silica gel with (10:1) methylenechloride-methanol followed by crystallization from methanol provided 0.61 g. (29%) of pure 4-Amino-7-(5-deoxy-beta-D-ribofuranosyl)-5-iodo-7H-pyrrolo[2,3-d]pyrimidine.

The following test results were obtained for the synthetically prepared compound: (m.p. 230°-232° C.), $^1$H NMR (Me$_2$SO-d$_6$) 1.28 (d, 3, J=6 Hz, CH$_3$), 3.88 (m, 2, C$_3$H and C$_4$H), 4.40 (m, 1, C$_2$H), 5.10 (d, 1, J=5 Hz, OH), 5.33 (d, 1, J=6 Hz, OH), 6.00 (d, 1, J=5 Hz, C$_1$H), 6.68 (C$_1$S, 2, NH), 7.62 (s, 1, C$_6$H), 8.13 (s, 1, C$_2$H). U.V. (0.1 NHCI) λmax 203 (19,450), 240 (18,850), 287 (8000), (H$_2$O) λmax 205 (21,000), sh 215 (18,300), sh (11,500), 283 (8200), (0.1 NKOH) λmax 282 (8400) sh 233 (11,400). IR(KBr) 3480 cm$^{-1}$ and 3300 cm$^{-1}$ (NH$_2$ and OH). Mass spectrum, m/e 377,376 (M+), 303,289,261,260,233. Elemental Analysis: calculated for C$_{11}$H$_{13}$N$_4$O$_3$I, C=35.12, H=3.48, N=14.90, I=33.74, found: C=35.07, H=3.50, N=14.61, I=34.14.

EXAMPLE 4

The compound prepared in Example 3 was administered orally to mice (male, 45-54 days old) at a dosage of 10 mg/kg and, after one hour, muscle relaxation was observed in two of three individuals. The effect at this dosage ceased to be observed at three hours after administration. Muscle relaxant activity was observed in all individuals at higher dosages ranging to and past the approximate LD50 level, which was 90 mg/kg. Similar muscle relaxant activity was noted when the drug was administered I.P., except that this effect was first observed in two of three individuals at a dosage of 3 mg/kg. Muscle relaxant activity continued to be observed to and past the approximate LD50 dosage of 78 mg/kg.

I claim:
1. A compound of the formula,

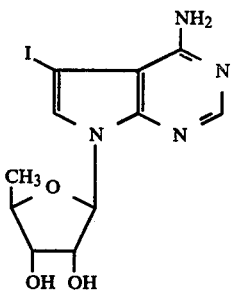

in substantially pure form.

2. A process to produce a compound of the formula

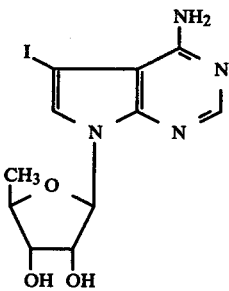

which comprises isolating the impure compound from red algae of the species Hypnea valendiae by methanol extraction and thereafter purifying the extract.

* * * * *